(12) United States Patent
Babayoff et al.

(10) Patent No.: US 7,946,846 B2
(45) Date of Patent: *May 24, 2011

(54) DENTAL IMAGING INSTRUMENT HAVING AIR STREAM AUXILIARY

(75) Inventors: Noam Babayoff, Holon (IL); Eldad Taub, Reut (IL); Avi Kopelman, Ramat Chen (IL)

(73) Assignee: Cadent Ltd., Or Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/703,085

(22) Filed: Feb. 7, 2007

(65) Prior Publication Data

US 2007/0134617 A1 Jun. 14, 2007

Related U.S. Application Data

(63) Continuation of application No. 10/174,271, filed on Jun. 18, 2002, now Pat. No. 7,255,558.

(51) Int. Cl.
*A61C 1/00* (2006.01)
(52) U.S. Cl. ......................................... 433/29
(58) Field of Classification Search .................. 433/29, 433/31, 99
See application file for complete search history.

(56) References Cited

U.S. PATENT DOCUMENTS

| | | | |
|---|---|---|---|
| 4,184,175 A | 1/1980 | Mullane, Jr. | |
| 4,201,200 A * | 5/1980 | Hubner | 433/29 |
| 4,575,805 A | 3/1986 | Moermann et al. | |
| 4,725,232 A | 2/1988 | Hatakeyama | |
| 4,952,149 A | 8/1990 | Duret et al. | |
| 5,115,307 A | 5/1992 | Cooper et al. | |
| 5,178,536 A | 1/1993 | Werly et al. | |
| 5,350,299 A | 9/1994 | Gallant | |
| 5,381,236 A | 1/1995 | Morgan | |
| 5,484,283 A * | 1/1996 | Franetzki | 433/116 |
| 5,737,084 A | 4/1998 | Ishihara | |
| 5,951,284 A * | 9/1999 | Lake | 433/31 |
| 6,254,597 B1* | 7/2001 | Rizoiu et al. | 606/13 |
| 6,263,234 B1 | 7/2001 | Engelhardt et al. | |
| 6,359,680 B1 | 3/2002 | Rubbert | |

(Continued)

FOREIGN PATENT DOCUMENTS

WO 00/08415 2/2000

OTHER PUBLICATIONS

Merriam-Webster definition of gas. Retrieved Mar. 4, 2009 from http://www.merriam-webster.com/dictionary/gas.*

*Primary Examiner* — Cris L Rodriguez
*Assistant Examiner* — Heidi M Eide
(74) *Attorney, Agent, or Firm* — The Nath Law Group; William L. Klima; Jiaxiao Zhang

(57) ABSTRACT

A dental instrument and method for imaging the three-dimensional topography of one or more teeth in the oral cavity of an individual is provided. The instrument includes a probe insertable into the oral cavity to receive the image of these surfaces which can then be processed. Combined with the probe is an auxiliary which projects an air stream toward the surface to be imaged by the probe and acts to evaporate and remove from these surfaces a liquid film coating formed by saliva and other fluids present in the or cavity, to render these surfaces dry and enhance their reflectivity and in doing so, provide clearer images.

18 Claims, 2 Drawing Sheets

U.S. PATENT DOCUMENTS

| | | |
|---|---|---|
| 6,386,867 B1 | 5/2002 | Durbin et al. |
| 6,443,729 B1 * | 9/2002 | Watson .......................... 433/30 |
| 6,468,076 B2 | 10/2002 | Kawamura |
| 6,697,164 B1 | 2/2004 | Babayoff et al. |
| 6,885,464 B1 * | 4/2005 | Pfeiffer et al. .................. 433/29 |
| 2001/0012605 A1 * | 8/2001 | Kawamura ...................... 433/29 |
| 2002/0055082 A1 | 5/2002 | Durbin et al. |

* cited by examiner

DENTAL IMAGING INSTRUMENT HAVING AIR STREAM AUXILIARY

This application is a continuation application of U.S. patent application Ser. No. 10/174,271 filed Jun. 18, 2002, now U.S. Pat. No. 7,255,558 the entire contents of which are incorporated in their entirety.

FIELD OF THE INVENTION

This invention relates generally to dental instruments for imaging the three-dimensional topography of teeth in a patient's oral cavity by means of a probe which projects a beam of light toward the surfaces of the teeth and receives reflections therefrom which are processed to derive the required data.

BACKGROUND OF THE INVENTION

It is a standard procedure in dental practice, when necessary to replace defective teeth in the oral cavity of a patient, to first make a cast impression of these teeth. A technician can from these impressions determine the three-dimensional parameters of a denture to replace the teeth.

It is known in order to avoid the need to make cast impressions to directly measure the teeth optically to obtain data for the computer-assisted design (CAD) or computer-assisted manufacture (CAM) of the replacement. In a typical instrument for this purpose, there is provided an optical probe projecting a light beam towards the surfaces of the teeth to be imaged.

The concern of the present invention is with those imaging instruments for direct optical measurement of a set of teeth which includes a probe to be inserted in the oral cavity to project a light beam toward the surfaces of the teeth and to receive light reflected therefrom which is then processed to obtain the digital data for determining the three-dimensional topology of the teeth.

One such instrument for obtaining the three-dimensional parameters of teeth in order to replace the teeth being imaged is disclosed in U.S. Pat. No. 4,575,805. In the patent, the probe takes the form of a scan bead which projects a scanning light beam toward the teeth surfaces.

Also disclosing an imaging instrument for the three-dimensional survey of teeth to obtain digital constructional data for the computer-controlled manufacture of a tooth replacement is U.S. Pat. No. 5,381,236. Another such instrument is an intra oral scanner disclosed in U.S. Pat. No. 6,359,680.

Of particular prior art interest is the imaging instrument disclosed in the PCT publication WO 00/08415 published 17 Feb. 2000 entitled "Imaging A Three-Dimensional Structure by Confocal Focusing an Array of Light Beams". This instrument is provided with a probe in the form of an endoscope which projects light beams toward the surfaces of the teeth to be imaged and receives light reflected therefrom which is processed to obtain the required digital data.

The problem of viewability encountered when using a dental imaging instrument whose probe projects a light beam to illuminate the surfaces of the teeth to be imaged is comparable to that experienced by eyes viewing these surfaces. If the eyes are heavily coated with a tear film, the resultant image will be blurred.

In the case of surfaces of teeth in an oral cavity containing mucous, saliva, and, in some instances, blood resulting from a dental procedure, the surfaces of the teeth are usually then coated with a liquid film composed of these constituents. This liquid film which impairs the ability of an imaging instrument to clearly view the teeth surfaces, cannot easily be dislodged, for the film is ionically attracted to the teeth surfaces and has a surface tension to protect the integrity of the film and resists its evaporation.

Under ideal circumstances, the surfaces of the teeth to be imaged should be free of liquid and perfectly clean and dry to obtain an optimal degree of reflectivity and image clarity. But this can only happen when the surface reflectivity exhibits a Lambert unit of luminescence. A Lambert unit is defined as the brightness of a perfect diffusing surface that radiates or reflects one lumen per square centimeter.

A saliva-mucous liquid film coating the teeth surfaces to be illuminated does not act as a perfect diffusing surface and therefore does not exhibit optimal reflectivity. And because this film adheres ionically to the tooth surfaces, it cannot just be washed away.

In common use by dentists is an air suction pipe (negative pressure) to suck out from the oral cavity saliva and mucous which interfere with the dental procedure then in progress. Also in common use is a pressured air pipe (positive pressure) which serves to blow away debris from the region in the oral cavity is working. These pipes must be manipulated by the dentist or his assistant so that the air stream (negative or positive) can be directed to the region of interest.

SUMMARY OF THE INVENTION

In the present invention, an auxiliary producing a positive or negative (suction) air stream is combined with a probe of an imaging instrument which is manipulated in the oral cavity to direct a light beam toward teeth surfaces to be illuminated, the auxiliary then also projecting the air stream in the same direction.

An auxiliary in accordance with the invention is combinable with the light-beam projecting probe of any existing dental imaging instrument adapted to survey the three-dimensional topography of teeth in the oral cavity.

It is thus the main object of this invention to provide a dental image acquisition and method for acquiring an image of the three-dimensional topography of a teeth segment in the oral cavity of a subject by means of a probe projecting a beam of light toward these surfaces, the probe being combined with an auxiliary which causes a stream of gas, typically air, to flow over the surfaces to be illuminated to dry these liquid-film coated surfaces to enhance their reflectivity to give rise to a clearer image of the teeth.

While the invention will be described, by way of example, in conjunction with a dental imaging instrument of the type disclosed in the above-identified PCT publication WO 00/08415, it is to be understood that it is applicable to any existing form of imaging instrument having a probe which projects a light beam to illuminate the surfaces of the teeth to be imaged.

Among the significant features of the invention, by which a dental imaging instrument is combined with an air stream auxiliary are the following:

A. The auxiliary can project the air stream towards the liquid film coating the surfaces of the teeth to be imaged at a velocity that disrupts the ionic bond between the liquid film and the teeth surfaces.
 B. The auxiliary air stream may be made to be in a pulsatory wave form to produce periodic bursts of air which effectively hammer away at the liquid film to dislodge it from the dental surfaces.

C. The air stream may be heated to a temperature level which promotes rapid evaporation of the liquid film coating the teeth surface, which level can be tolerated by the patient.

D. The heated air stream may act to fully dry the teeth surfaces to enhance their reflectivity and in doing so produce clearer images of the teeth.

E. The auxiliary from which the air stream is projected may be integrated with the probe from which a light beam is projected to illuminate the surfaces of the teeth to be imaged, whereby the air stream is focused on the surfaces to provide rapid drying thereof.

The invention thus provides, by one of its aspects, a dental instrument for imaging the three-dimensional surface topography of a teeth segment consisting of one or more adjacent teeth in the oral cavity of an individual, e.g. in order to acquire digital data regarding the parameters of a replacement or prosthesis for a missing or broken tooth. The instrument includes a probe insertable into the oral cavity to capture an image of the teeth segment. The probe typically also projects a light beam toward the surfaces of the teeth to be imaged. Alternatively, the illumination may also be an independent light source. The captured image is then conveyed to a processor to obtain the required data. Combined with the probe is an auxiliary which by one embodiment projects an air stream toward the surfaces to be imaged by the probe. The air stream acts to evaporate and remove from these surfaces a liquid film coating formed by saliva and other fluids present in the oral cavity. The surfaces thereby become dry and this enhances their reflectivity, to yield clearer images. By another embodiment, the auxiliary includes a suction arrangement that induces an air stream in an opposite direction that may yield a result comparable to that achieved with the embodiment discussed above. In this matter the film coating is sucked away from the teeth.

By another aspect, there is provided a method for imaging the three-dimensional surface topography of a teeth segment. It comprises bringing a probe into proximity of the teeth to be imaged and acquiring the image. The method is characterized in that while acquiring the teeth image causing a stream of gas to flow over the surface of the teeth to be imaged.

In accordance with one embodiment of the invention, said auxiliary induces two air streams, one flowing over the surface of the teeth segment to be imaged, while the other flows over the external optical sensing surface, namely, the external surface of the optical system that acquires the image. In some imaging techniques, e.g. one that makes use of the optical sensing surface such as that disclosed in PCT Publication WO/00/08415, the probe needs to be inserted into the oral cavity and brought into proximity with the teeth to be imaged. In this case, the optical sensing surface may also become coated with a liquid film formed from aerosol particles that exist in the oral cavity or liquid vapor that condenses on the sensing surface.

An optical probe making use of confocal optics is a preferred embodiment in accordance with the invention.

BRIEF DESCRIPTION OF THE DRAWINGS

For a better understanding of the invention as well as other objects and features thereof, reference is made to the annexed drawings in which.

DETAILED DESCRIPTION OF THE INVENTION

As explained above, a dental imaging instrument of the type disclosed in PCT Publication No. WO 00/08415 or others in which a probe directs a beam of light toward the surfaces of the teeth to be imaged and picks up light reflected from these surfaces, is unable to obtain clear images because the liquid film which coats these surfaces degrade their reflectivity.

A liquid film composed mainly of saliva and mucous present in the oral cavity as well as blood, is ironically adhered to the teeth surfaces and cannot therefore be easily dislodged. The present invention combines the imaging probe with an auxiliary which directs an air stream toward the surface to evaporate the film thereon even though the evaporative process is resisted by the surface tension of the film.

The rate at which liquid is evaporated by a stream of air flowing over its surface depends on the temperature of the air and its velocity. Hence, even when the temperature is fairly high, should the air stream then pass slowly over the liquid surface, the surface tension which acts as a skin covering the liquid will not be disrupted.

The external optical surfaces of the optical sensing probe have to be kept clean of any particles, film, etc., so as to retain good optical qualities required in order to be able to acquire a high quality image. The problem, however, is that the probe needs to be inserted into the oral cavity and consequently such optical surfaces may become coated, particularly by a liquid film, as a result of aerosol particles that exist in the oral cavity or liquid vapor that condenses on such surfaces. Thus, in accordance with one embodiment, the auxiliary provides also a gas stream that flows over such optical surfaces so as to clean such surfaces from any liquid film or droplets that may form thereon.

Figure 1:
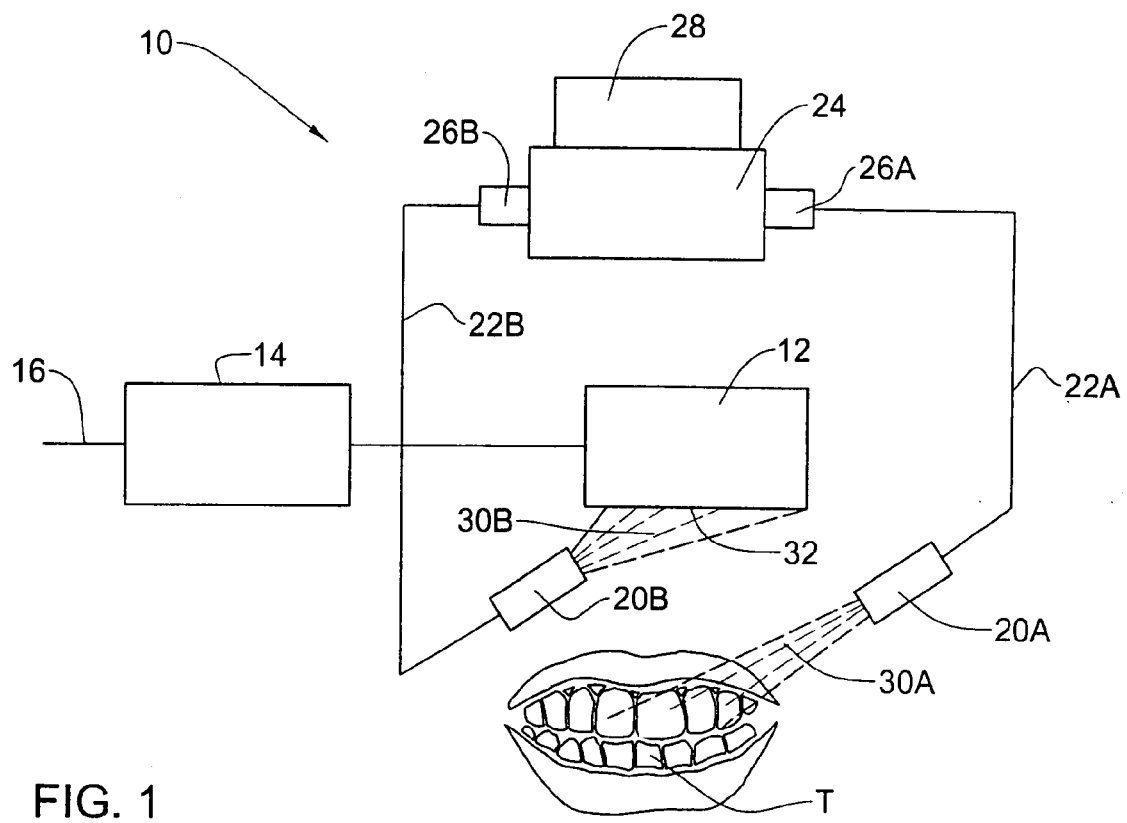
FIG. 1 shows a schematic illustration of an instrument with an auxiliary assembly in accordance with the invention.

Reference is first being made to FIG. 1, showing, in a schematic manner, an optical imaging instrument generally designated 10 that includes an optical probe 12 that can be inserted into the oral cavity and brought into proximity to teeth T and imaging optics and electronics assembly represented by block 14. Block 14 is coupled, through line 16 to an image analysis and data storage computer system (not shown).

The probe and the optical/electronic system may be that disclosed in PCT publication WO 00/08415, now issued as U.S. Pat. No. 6,697,164, the contents of which is incorporated herein by reference.

Probe 12 is associated with two nozzles 20A and 20B, each of which is linked through corresponding lines 22A and 22B to a source of pressurized gas 24. Source 24 may be a pressurized gas container or may be a compressor. The source of pressurized gas will typically be located outside the handheld probing instrument (not shown) that houses probe 12 and the optic/electronic assembly 14.

Each of lines 20A and 20B includes also a corresponding flow control valve 26A and 26B. It should be noted that rather than having independent lines, the two lines may combine through a manifold arrangement into a single line that leads to source 24.

In some embodiments of the invention, the gas is heated and a heating source 28 associated with the source of pressurized gas 24 may be provided. In other embodiments, rather than heating the gas at source, the gas may pass through a heat exchanger for online heating before reaching nozzles 20A and 20B. As will be appreciated, the gas is typically air although other gasses such as nitrogen, oxygen, and others.

Nozzle 20A is designed to eject a stream of gas 30A towards a segment of the teeth that is to be imaged. The rapid flow of gas, at times heated, over these surfaces, removes the liquid film which otherwise coats the surface of the teeth.

In one preferred embodiment of the invention, a second nozzle 20B is provided which directs the flow of gas 30B towards the optical surface 32 of probe 12. In this way a liquid film or droplets which would otherwise form on surface 32 are removed.

It should be noted that the instrument may at times be provided with more than one nozzle, such as nozzle 20A or nozzle 20B.

The above description was made in reference to an embodiment where a source of pressurized gas 24 causes a positive flow of gas towards the surface of the teeth T and the surface 32 of probe 12. In other embodiments of the invention, source 24 may be a suction pump giving rise to a negative-pressure air stream, namely from the surface towards the nozzles. A negative air stream will cause air in the oral cavity to flow over the teeth's surfaces, as well as over the optical surface 32 of probe 12 causing the removal of the liquid from such surfaces in this manner. One advantage of negative-pressure air stream is that it will also suck out the vapor evaporated from the liquid film.

Figure 2:
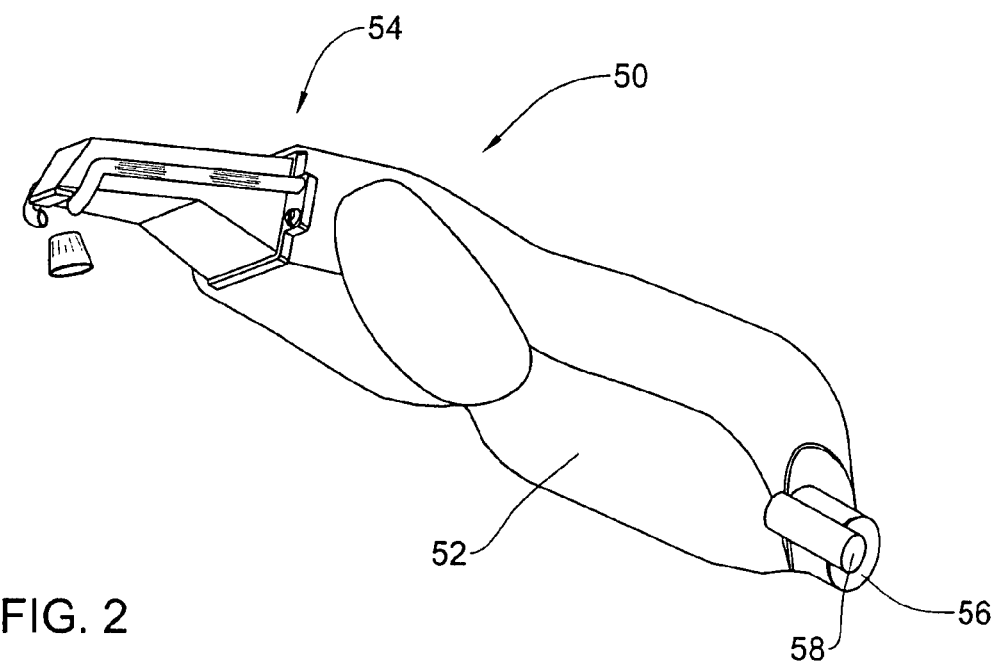
FIG. 2 is a perspective view of a dental imaging instrument incorporating an auxiliary assembly in accordance with the invention.
Figure 3:
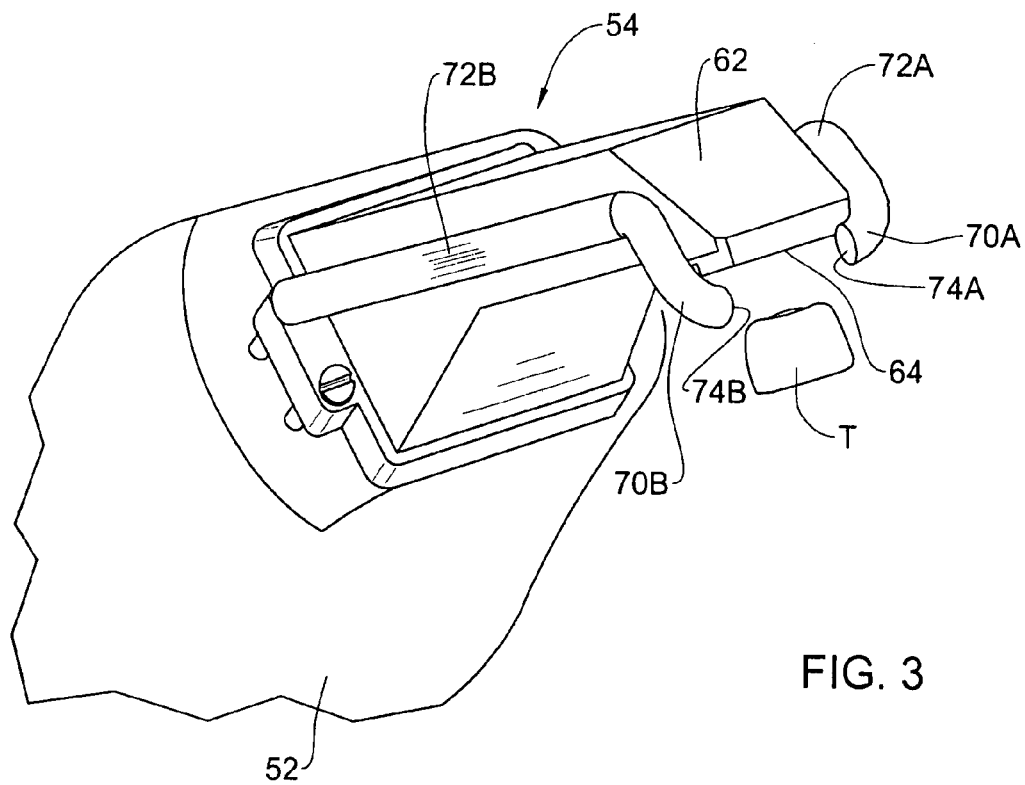
FIGS. 3 and 4 are close-up perspective views, from two different angles, of the front probing portion of the instrument of FIG. 2.
Figure 4:
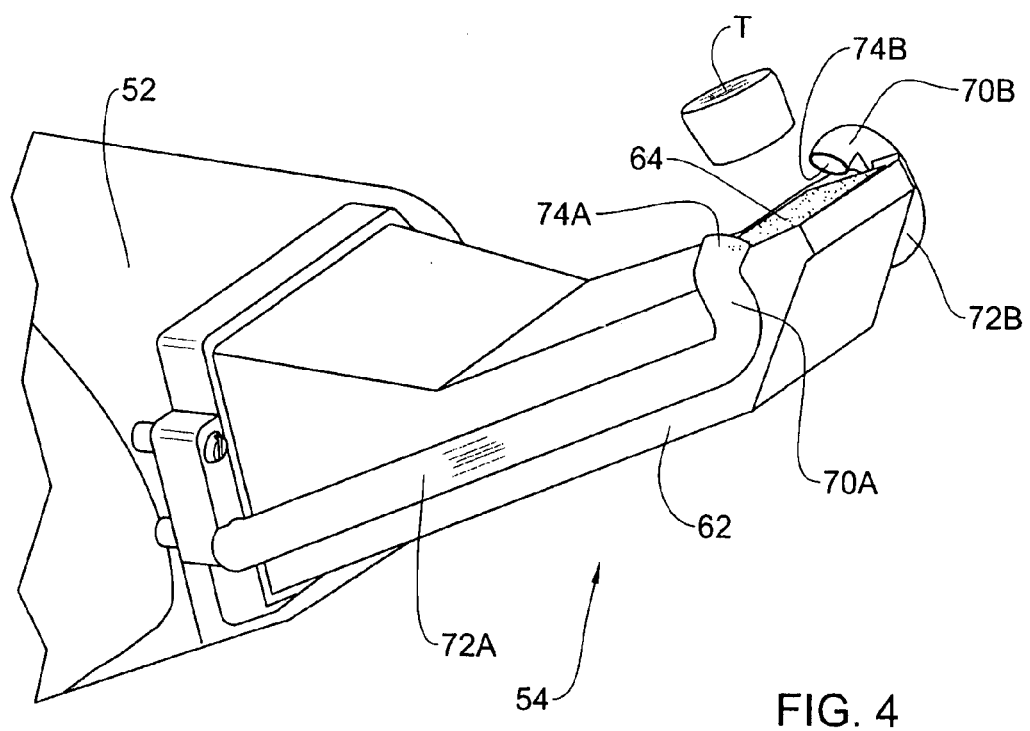

Reference is now being made to FIGS. 2, 3 and 4, showing a handheld probing instrument in accordance with an embodiment of the invention. Instrument 50 has a handle 52 and a head 54. Handle 52 houses the optics electronic assembly that is linked, through connector 56, to an image processing and image storage computers (not shown). Also shown at the rear of handle 52 is a conduit 58 for connecting to a source of pressurized gas (or a vacuum source in accordance with other embodiments of the invention).

The structure of head 54 is best seen in FIGS. 3 and 4. Head portion 54 includes an optical probe 62 designed in the manner shown in FIGS. 2A and 2B of the aforementioned PCT publication WO 00/00815. Optical probe 62 has an external probing glass surface 64 which in use is brought proximal to the teeth to be imaged. For the purpose of illustration, an image of a single tooth T in isolation being proximal and opposite probing glass surface 64, is shown.

Situated on two sides of probe 62 are nozzles 70A and 70B situated at the end of respective straight and rigid tubes 72A and 72B which are linked, through tubings within the handle/housing 52, to gas conduit 58. As can be seen, the opening 74A of nozzle 70A faces the surface to be imaged while opening 74B of nozzle 70B faces glass surface 64. By projecting air out of openings 74A and 74B of nozzles 70A and 70B surface 64 and surface of the tooth will be clean of liquid films or droplets.

In accordance with another embodiment rather than ejecting gas out of these nozzles in a positive ejection fashion, a suction arrangement is provided for sucking air from such surfaces with a similar resulting effect.

The invention claimed is:

1. A dental instrument configured for determining three dimensional (3D) topography of a teeth segment comprising one or more teeth, said instrument comprising:
an imaging optics and electronics assembly configured for projecting incident beams of light toward said teeth segment and for capturing an image formed by the incident light beams that are reflected from said teeth segment;
a processor, processing said captured image to generate therefrom the 3D topography; and
a handheld probe comprising:
a probe head,
an external optical sensing face at a distal end of said probe head, placed proximal to said teeth segment when in use, wherein said incident beams of light are directed toward said teeth segment through said external optical sensing face and said incident light beams reflected from said teeth segment are received through said external optical sensing face, and
two auxiliary nozzles that directs a first stream of gas to or from said external optical surface and a second stream of gas towards said teeth segment, wherein said two auxiliary nozzles are directly coupled to said handheld probe,
wherein said dental instrument further comprises a heat source configured for providing said first stream of gas at a temperature above body temperature.

2. The instrument according to claim 1, wherein the first stream of gas is a positive stream emitted towards said external optical surfaces.

3. The instrument according to claim 2, wherein said gas is air.

4. The instrument according to claim 1, wherein the first stream of gas is under negative-pressure.

5. The instrument according to claim 4, wherein at least one auxiliary nozzle is coupled to a vacuum pump.

6. The instrument according to claim 1, wherein the auxiliary nozzles include a pair of nozzles mounted on opposite sides of the probe.

7. The instrument according to claim 6, wherein the nozzles are oriented so that one nozzle produces a gas stream on the teeth segment, and the other nozzle produces a gas stream over the external optical surface of the probe.

8. The instrument according to claim 6, wherein the nozzles are coupled to an air compressor.

9. The instrument according to claim 1, wherein said first stream of gas is a pulsating stream of gas.

10. The instrument according to claim 1, wherein said probe head has a proximal end having a larger cross-section than the distal end thereof.

11. The instrument according to claim 1, wherein said first stream of gas is directed laterally across said sensing face with respect to a longitudinal axis of the probe head.

12. The dental instrument of claim 1, comprising:
an illumination unit configured for generating said incident beams and projecting said incident beams of light toward said teeth segment; and
an optical detector configured for receiving said incident light beams reflected from said teeth segment.

13. A method for determining a three-dimensional (3D) surface topography of a teeth segment comprising one or more teeth, the method comprising:
manually bringing an external optical sensing surface of a handheld probe into proximity of the teeth segment;
directing incident beams of light through said external optical sensing face toward surfaces of said teeth segment;
picking up light reflected from said surfaces via said external optical sensing face; and
processing said picked up light to provide digital data associated with said 3D topography;
wherein, while picking up light reflected from said surfaces, causing a first stream of gas to flow with respect to said external optical sensing face and directing a second stream of gas towards said teeth segment, the first stream of gas is at a temperature above body temperature.

14. The method according to claim 13, wherein the first stream of gas is a positive stream emitted towards said external optical sensing face.

15. The method according to claim 14, wherein said gas is air.

16. The method according to claim 13, wherein the first stream of gas is under negative-pressure.

17. The method according to claim 13, wherein said first stream of gas and said second stream of gas produce two intersecting sector-shaped gas streams.

18. The method according to claim 13, wherein said first stream of gas is directed laterally across said sensing face with respect to a longitudinal axis of the probe head.

\* \* \* \* \*

UNITED STATES PATENT AND TRADEMARK OFFICE
CERTIFICATE OF CORRECTION

| | | |
|---|---|---|
| PATENT NO. | : 7,946,846 B2 | Page 1 of 1 |
| APPLICATION NO. | : 11/703085 | |
| DATED | : May 24, 2011 | |
| INVENTOR(S) | : Noam Babayoff et al. | |

It is certified that error appears in the above-identified patent and that said Letters Patent is hereby corrected as shown below:

In the Claims:

Column 6, Claim 1, Line 10, please delete "directs" and insert --direct--.

Signed and Sealed this
Eleventh Day of October, 2011

David J. Kappos
*Director of the United States Patent and Trademark Office*